United States Patent [19]

Wild et al.

[11] Patent Number: 5,120,849
[45] Date of Patent: Jun. 9, 1992

[54] PREPARATION OF O-SUBSTITUTED HYDROXYLAMINES

[75] Inventors: Jochen Wild, Deidesheim; Norbert Goetz, Worms; Wolfgang Will, Kirchheim; Rolf-Dieter Kohler, Edingen-Neckarhausen; Peter Plath, Frankenthal, all of Fed. Rep. of Germany

[73] Assignee: BASF Aktiengesellschaft, Ludwigshafen, Fed. Rep. of Germany

[21] Appl. No.: 638,144

[22] Filed: Jan. 9, 1991

Related U.S. Application Data

[63] Continuation of Ser. No. 423,670, Oct. 19, 1989, abandoned, which is a continuation of Ser. No. 304,857, Jan. 31, 1989, abandoned, which is a continuation of Ser. No. 45,551, May 4, 1987, abandoned.

[30] Foreign Application Priority Data

May 7, 1986 [DE] Fed. Rep. of Germany ....... 3615473

[51] Int. Cl.⁵ .................................... C07C 211/02
[52] U.S. Cl. .................................... 546/334; 548/143; 548/465; 548/475; 548/517; 548/545; 546/319; 546/321; 549/59; 549/75; 549/472; 549/492; 558/418; 558/452; 560/155; 564/198; 564/300; 564/498
[58] Field of Search ............ 564/300, 498, 198; 546/334; 549/75, 492; 548/143; 558/418, 452; 560/155

[56] References Cited

U.S. PATENT DOCUMENTS

| | | | |
|---|---|---|---|
| 3,262,978 | 7/1966 | Robertson | 564/300 |
| 3,278,583 | 10/1966 | Berger | 564/300 X |
| 3,280,171 | 10/1966 | Berger | 564/300 X |
| 3,342,678 | 9/1967 | Berger | 564/300 X |
| 4,544,755 | 10/1985 | Hagen et al. | 564/166 |
| 4,863,636 | 5/1989 | Chang et al. | 560/37 |

FOREIGN PATENT DOCUMENTS

| | | |
|---|---|---|
| 3615473 | 11/1987 | Fed. Rep. of Germany . |
| 8248059 | 10/1976 | Japan . |
| 0112945 | 6/1984 | Japan .................. 564/300 |
| 1331203 | 9/1973 | United Kingdom . |

OTHER PUBLICATIONS

Millar et al., "Sidgwick's Organic Chemistry of Nitrogen" 3rd Ed. pp. 96-97 (1968).
Delia et al. (1983) J. of Heterocyclic Chem. 20: 145-147.
Houben-Weyl, vol. 10/1, pp. 1181-1201.

*Primary Examiner*—Donald G. Daus
*Attorney, Agent, or Firm*—Keil & Weinkauf

[57] ABSTRACT

O-substituted hydroxylamines (I)

$$H_2N-O-CH_2-R \qquad (I)$$

where R is H or an organic radical, and their salts are prepared by reacting a cyclic imidoether II of a 1,4- or 1,5-dicarboxylic acid, the said imidoether containing an ether group $-O-CH_2-R$, with a basic compound by a method in which a primary aliphatic aminoalcohol III is used as the basic compound and the compound I is, if required, converted to its salts.

8 Claims, No Drawings

PREPARATION OF O-SUBSTITUTED HYDROXYLAMINES

This application is a File Wrapper Continuation of Ser. No. 423,670, filed Oct. 19, 1989, now abandoned; which is in turn a File Wrapper Continuation of Ser. No. 304,857, filed Jan. 31, 1989, now abandoned; which is in turn a File Wrapper Continuation of Ser. No. 045,551, filed May 4, 1987, now abandoned.

The present invention relates to a novel process for the preparation of O-substituted hydroxylamines of the general formula I

$$H_2N-O-CH_2-R \qquad (I)$$

where R is hydrogen or an organic radical, and their inorganic or organic salts by reacting a cyclic imidoether II

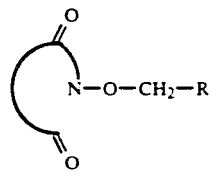
(II)

of a 1,4- or 1,5-dicarboxylic acid, the said imidoether containing an ether group —O—CH$_2$—R, with a basic compound, wherein the basic compound used is a primary aliphatic aminoalcohol III

$$H_2N-A-OH \qquad (III)$$

where —A— is a divalent aliphatic radical, and the compound I is, if required, then converted to its salts.

The present invention furthermore relates to novel O-substituted hydroxylamines of the general formula IV

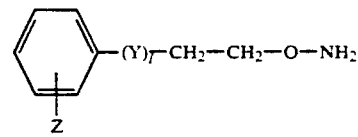
(IV)

where Y is oxygen or sulfur, Z is $C_1$-$C_8$-alkyl, halogen or $CF_3$ and L is 0 or 1, and their inorganic or organic salts which are intermediates for crop protection agents.

It is generally known that substitution of a hydroxylamine leads to reaction at the amine nitrogen. In order to effect substitution at the hydroxyl group, it is generally necessary to block the amine function. The entire synthesis may therefore be divided into three steps:
protection of the hydroxylamine at the nitrogen
substitution at the free oxygen
elimination of the protective group.

For reasons relating to cost, four N-blocked hydroxylamine derivatives are particularly suitable for industrial syntheses:
cyclic N-hydroximides, especially N-hydroxyphthalimide
ketoximes, especially acetoxime
hydroxyurethanes
hydroxamic acids and their derivatives, e. g. ester oximes.

As a rule, substitution of these hydroxylamine derivatives at the oxygen does not present any problems. In contrast, elimination of the protective groups and isolation and purification of the substituted hydroxylamines are much more problematic.

It is known from Houben/Weyl, Vol. 10/1, page 1181 et seq, that all four O-alkyl derivatives can be cleaved by hydrolysis in an aqueous mineral acid, and in some cases also in aqueous alkali. Under these reaction conditions, however, side reactions take place, so that these methods of cleavage can be used only to a restricted extent for the preparation of simple and very stable O-substituted hydroxylamines.

Houben/Weyl, Vol. 10/1, page 1181 et seq, also discloses that phthalimidoethers can be cleaved under substantially milder conditions by nucleophiles, in particular hydrazines and amines, in an anhydrous medium.

Cleavage with primary amines is disclosed in German Patents 2,206,890 and 2,241,035, but is not widely used since separation of the product from excess amine and in particular from the N-alkyl phthalimide presents considerable problems.

The hydrazinolysis of phthalimidoethers for the preparation of O-substituted hydroxylamines is a frequently used laboratory method. However, in addition to the precipitated phthalic hydrazide, the basic compound N-aminophthalimide is also formed; separation of the latter from the end product, which is likewise basic, presents very considerable problems.

Great difficulties are also encountered in carrying out this reaction on an industrial scale. The resulting sparingly soluble phthalic hydrazide separates out as a bulky precipitate, so that large amounts of solvents and large reaction kettles are required for handling it. The acute toxicity and the high price of hydrazine are further obstacles to commercial use.

Furthermore, Japanese Published Application 82/48059 discloses that alkyl-, alkenyl- and alkynyl-phthalimidoethers can be cleaved with aqueous hydroxylamine sulfate solution. Separation of the O-substituted hydroxylamines from hydroxyphthalimide by distillation merely gives aqueous solutions of the O-substituted hydroxylamines, so that this process cannot be used for the preparation of isolated (anhydrous) O-alkylhydroxylamines or their salts.

However, in order to use the O-substituted hydroxylamines as intermediates, it is desirable to react them further in isolated (anhydrous) form or in organic solvents, if necessary in an anhydrous medium.

The distillative purification required in this process gives only low molecular weight O-substituted hydroxylamines which can be distilled and are thus stable.

It is an object of the present invention to provide a process which does not have the above disadvantages.

We have found that this object is achieved by a process for the preparation of O-substituted hydroxylamines of the general formula I and their inorganic and organic salts by reacting a cyclic imidoether II of a 1,4- or 1,5-dicarboxylic acid, the said imidoether containing an ether group —O—CH$_2$—R, with a basic compound, wherein a primary aliphatic aminoalcohol III is used as the base, and the compound I is, if required, then converted to its salts.

We have also found that water-insoluble compounds I are advantageously prepared using an excess of the aminoalcohol III over the imidoether II and are isolated by extracting the water-soluble components with water.

We have also found novel O-substituted hydroxylamines of the formula IV.

The cyclic N-hydroximides of the parent 1,4- or 1,5-dicarboxylic acids, which are required to prepare the compounds II, are either known or can be obtained by reacting the cyclic anhydrides with hydroxylamine by known methods. Examples of suitable cyclic N-hydroximides are:

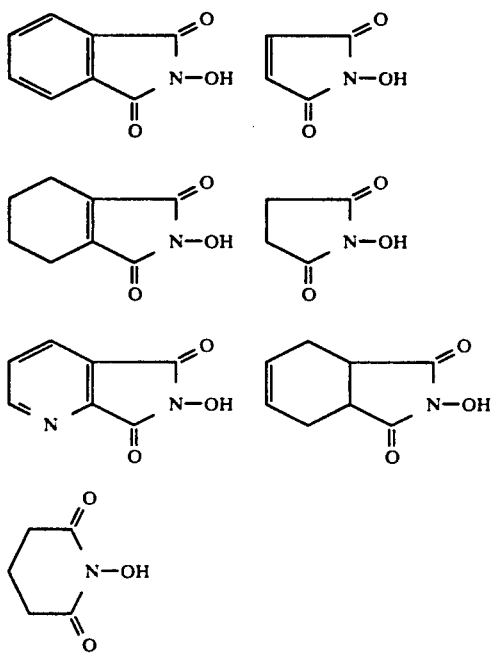

The cyclic N-hydroximides can be converted to the corresponding imidoethers II with halides or sulfonates R—CH$_2$—X in the presence of an acid acceptor:

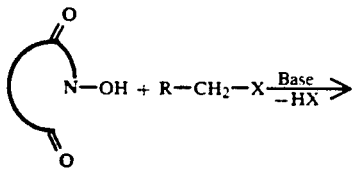

X is, for example, Cl, Br, mesyl, benzenesulfonyl or tosyl.

Observations to date have shown that the success of the process does not appear to be dependent on the nature of the radicals R provided that these radicals do not carry any reactive groups, such as oxo or acyl halide groups.

R is, for example, hydrogen, alkyl, such as methyl, ethyl, n-propyl, isopropyl, n-butyl, isobutyl, tert-butyl, hexyl, octyl, decyl, dodecyl or tridecyl, alkenyl, such as ethenyl, 1-propenyl, 2-propenyl, butenyl or hexenyl, alkynyl, such as ethynyl or propargyl, alkoxyalkyl, such as methoxymethyl, methoxyethyl, methoxypropyl, ethoxymethyl, ethoxyethyl or ethoxybutyl, haloalkyl, such as trifluoromethyl, fluoromethyl, 1-fluoroethyl or chloroethyl, haloalkenyl, such as chloroethenyl, fluoroethenyl or bromoethenyl, cycloalkyl, such as cyclopropyl, cyclopentyl, cyclohexyl or cyclooctyl, halocycloalkyl, such as 2,2-dichlorocyclopropyl, aryl, such as phenyl or naphthyl, substituted phenyl, such as p-fluorophenyl, p-tolyl, p-nitrophenyl, p-cyanophenyl, m-chlorophenyl, p-methoxyphenyl, m-trifluoromethylphenyl, p-chlorophenyl, 3,4-dichlorophenyl or 2,6-dichlorophenyl, hetaryl, such as 3-pyridyl, 5-isopropyl-1,3,4-oxadiazol-2-yl, 5-chlorothien-2-yl or 5-methylthien-2-yl, benzyl, substituted benzyl, such as p-fluorobenzyl, p-methylbenzyl, p-nitrobenzyl, p-cyanobenzyl, o-chlorobenzyl, m-chlorobenzyl or p-chlorobenzyl, phenoxyalkyl, such as phenoxymethyl, phenoxyethyl, phenoxybutyl or phenoxyhexyl, substituted phenoxyalkyl, such as o-fluorophenoxymethyl, m-trifluoromethylphenoxymethyl, o- and m-chlorophenylmethyl, o-fluorophenoxyethyl, m-trifluoromethylphenoxyethyl and o- and m-chlorophenoxyethyl, halocycloalkylalkyl, such as 2,2-dichlorocyclopropylmethyl and 2-chlorocyclopentylethyl, aryloxyalkyl, such as 2-naphthyloxymethyl and 2-naphthyloxyethyl, phenylthioalkyl, such as phenylthiomethyl, phenylthiobutyl and phenylthiohexyl, substituted phenylthioalkyl, such as m-chlorophenylthiomethyl and m-chlorophenylthioethyl, dialkoxyalkyl, such as dimethoxyethyl, diethoxymethyl, diethoxyethyl, diethoxybutyl and diethoxyhexyl, phenylalkyl, such as phenylethyl, phenylpropyl, phenylbutyl and phenylhexyl, substituted phenylalkyl, such as p- or m-chlorophenylethyl, carboxylate, such as methylcarboxylate, ethylcarboxylate, isobutylcarboxylate and tert-butylcarboxylate, carboxamide, N-alkylcarboxamide, N,N-dialkylcarboxamide, such as N,N-dimethylcarboxamide, nitrile, cyanoalkyl, such as cyanomethyl or 2-cyanoethyl, and cyclic ether groups, such as 2-tetrahydrofuryl, 2-tetrahydrofurylmethyl or 2-tetrahydrofurylbutyl.

Particularly suitable primary aliphatic aminoalcohols III are compounds III $$H_2N—A—OH \qquad (III)$$

where —A— is —(CH$_2$)$_n$, —CH$_2$—CH$_2$(CH$_3$)CH$_2$— or —(CH$_2$CH$_2$O)$_m$—CH$_2$CH$_2$—, m is 1 or 2 and n is 2, 3 or 4. Especially useful compounds III are those in which —A— is —CH$_2$—CH$_2$—, —CH$_2$—CH$_2$—CH$_2$—, —CH$_2$—CH$_2$—CH$_2$—CH$_2$, —CH$_2$—CH(CH$_3$)CH$_2$—, —CH$_2$CH$_2$OCH$_2$CH$_2$— or —CH$_2$CH$_2$O—CH$_2$CH$_2$O—CH$_2$CH$_2$—.

Preferred aminoalcohols III are 3-aminopropan-1-ol, 4-aminobutan-1-ol, 2-(2-aminoethoxy)-ethanol and especially 2-aminoethanol.

The compounds IV according to the invention can be prepared by the novel process described above. Y is oxygen or sulfur, preferably oxygen, Z is C$_1$-C$_8$-alkyl, preferably C$_1$-C$_4$-alkyl, particularly preferably methyl or ethyl, halogen, preferably fluorine, chlorine or bromine, particularly preferably chlorine, or trifluoromethyl, and l is 0 or 1, preferably 0.

Depending on the structure of the radical R, there are essentially two possible reaction procedures for the preparation of the O-substituted hydroxylamines by reacting an imidoether II with an aminoalcohol III:

a) For water-insoluble O-substituted hydroxylamines I

For this purpose, the imidoether II is introduced into excess aminoalcohol III and the mixture is stirred at from 20° to 100° C., preferably from 40° to 70° C., until cleavage is complete. The mixture is poured into water, the excess aminoalcohol and the cleavage product going into solution. The O-substituted hydroxylamine I is either filtered off under suction or extracted from the aqueous phase with a suitable solvent.

Solvents which are suitable for the extraction are chlorohydrocarbons, such as methylene chloride, chloroform, carbon tetrachloride, 1,1,1-trichloroethane, hexachloroethane, tetrachloroethylene and chlorobenzene, ethers, such as diethyl ether, methyl tert-butyl ether and diisopropyl ether, carboxylates, such as methyl acetate and ethyl acetate; methylene chloride, ethyl acetate and methyl tert-butyl ether are particularly preferred.

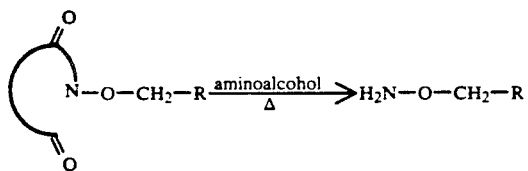

b) For partially and completely water-soluble O-substituted hydroxylamines I

They can be particularly advantageously isolated in the form of their salts by partially or completely dissolving the imidoether II in an inert solvent and adding an equimolar amount or a slight excess, from 0.01 to 30, preferably from 5 to 15, mol %, of the aminoalcohol III. This gives a homogeneous reaction mixture, which is stirred at from 20° to 100° C., preferably from 40° to 70° C., until the cleavage is complete. The cleavage product is filtered off under suction, and the filtrate is treated with an anhydrous acid, the salt of the O-substituted hydroxylamine being obtained in high purity and yield.

Among the gaseous acids, dry hydrogen chloride is particularly preferred. Liquid acids, or solid acids dissolved in one of the abovementioned inert solvents, are added in equimolar amounts. Anhydrous sulfuric acid, acetic acid, propionic acid, phosphoric acid, malonic acid and benzoic acid are preferred, anhydrous oxalic acid being particularly preferred.

Suitable inert solvents are chlorohydrocarbons, such as methylene chloride, chloroform, carbon tetrachloride, 1,1,1-trichloroethane, hexachloroethane, tetrachloroethylene and chlorobenzene, ethers, such as diethyl ether, diisopropyl ether, methyl tert-butyl ether, tetrahydrofuran and dioxane, carboxylates, such as methyl acetate and ethyl acetate, hydrocarbons, such as toluene and petroleum ether. Ethers, for example diethyl ether, diisopropyl ether, methyl tert-butyl ether, tetrahydrofuran and dioxane, chlorohydrocarbons, such as methylene chloride and chloroform and carboxylates, e.g. ethyl acetate, are preferred.

The advantage of the novel process over the conventional methods of the preparation of O-substituted hydroxylamines I is that the synthesis can be used widely, in particular for the preparation of O-substituted hydroxylamines of the general formula I which possess sensitive radicals R.

Cleavage of the cyclic imidoethers II takes place readily and without side reactions. The cleavage product is particularly readily separated from the O-substituted hydroxylamine I.

The novel process makes it possible to prepare, in good yields, complex or sensitive O-substituted hydroxylamines I, e.g. phenylethoxyamines or phenoxyethoxyamines, which could not be obtained by conventional methods.

Overall, the novel process is distinguished by simple steps and convenient handling of the reaction mixtures, since no bulky precipitates occur, allowing the synthesis to be carried out in a simple manner on a large industrial scale too.

The O-substituted hydroxylamines I and IV and their salts are important intermediates, in particular for the preparation of crop protection agents (DE-A-31 21 355 and EP-A-01 42 741).

EXAMPLES

Unless stated otherwise, the ¹H NMR spectra were recorded in perdeuterodimethyl sulfoxide (D₆-DMSO) as solvent, using tetramethylsilane as an internal standard. The chemical shifts are stated in $\delta$ [ppm] in each case. The following abbreviations are used for the signal structure:

s = singlet,
d = doublet,
t = triplet,
q = quartet and
m = multiplet.

PREPARATION OF THE CYCLIC IMIDOETHER II 2.3 moles of the alkyl chloride (or alkyl bromide) are added to 2.3 moles of cyclic N-hydroximide and 214 g of potassium carbonate in 2.3 l of N-methylpyrrolidone at 40° C. The mixture is stirred for 4 hours at 50° C. and then poured into ice water, and the product is filtered off under suction and washed with water.

The results are summarized in Table 1.

TABLE I

| Intermediate No. | R | | m.p. [°C.] | ¹H-NMR | Yield [%] |
|---|---|---|---|---|---|
| II/1 | —CH(OCH₂CH₃)₂ | phthalimide structure | | 1.10(t), 1.10(t) 3.48-3.74(m) 4.15(d), 4.86(t) 7.82(s) | 88 |
| II/2 | o-F—C₆H₄—O—CH₂— | " | 119-121 | | 90 |
| II/3 | o-Cl—C₆H₄—CH₂— | " | 73-74 | | 78 |

TABLE I-continued

| Intermediate No. | R | | m.p. [°C.] | $^1$H-NMR | Yield [%] |
|---|---|---|---|---|---|
| II/4 | 2-Tetrahydrofuryl | " | 98–100 | | 88 |
| II/5 | —CH$_2$—O-(2-Naphthyl) | " | >230 | | 87 |
| II/6 | m-CF$_3$—C$_6$H$_4$—O—CH$_2$— | " | 175–176 | | 82 |
| II/7 | Cyclopropyl | " | 78–80 | | 86 |
| II/8 | p-Cl—C$_6$H$_4$—CH$_2$— | " | | 3.06(s), 4.36(s), 7.37(d), 7.83(d), 7.87(s) | 86 |
| II/9 | —CH$_2$—CH$_2$—O—CH$_2$—CH$_3$ | " | | 1.11(t), 1.93(t), 3.44(q), 3.55(t), 4.23(t), 7.87(s) | 81 |
| II/10 | 2,2-Dichlorocyclopropyl | " | | 1.53(t), 1.84(dd), 2.22–2.31(m), 4.11(dd), 4.50(dd), 7.90(s) | 87 |
| II/11 | o-Cl—C$_6$H$_4$—O—CH$_2$— | " | 127–129 | | 99 |
| II/12 | m-Cl—C$_6$H$_4$—O—CH$_2$— | " | | 4.33(t), 4.53(t) 6.84–7.03(m), 7.29(t) 7.87(s) | 97 |
| II/13 | —CH$_2$F | " | Oil | | 70 |
| II/14 | m-Cl—C$_6$H$_4$—S—CH$_2$— | 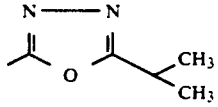 | 73–75 | | 80 |
| II/15 | Cyclohexyl | " | 91–93 | | 95 |
| II/16 | —CH$_2$—CH$_2$CN | " | 103–105 | | 89 |
| II/17 | —CONH$_2$ | " | 190–192 | | 81 |
| II/18 | —C≡C—CH$_3$ | " | Öl | | 72 |
| II/19 | 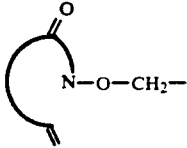 | " | 115–116 | | 97 |
| II/20 | 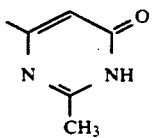 | " | 240–241 | | 85 |
| II/21 | 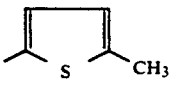 | " | Öl | | 75 |
| II/22 | trans-CH=CHCl | " | 132–134 | | 99 |
| II/23 | cis-CH=CHCl | " | | | 98 |
| II/24 | —COOC(CH$_3$)$_3$ | " | 146–147 | | 96 |
| II/25 | p-F—C$_6$H$_4$— | " | 160–162 | | 99 |
| II/26 | p-CH$_3$—C$_6$H$_4$— | " | 144–146 | | 100 |
| II/27 | p-NO$_2$—C$_6$H$_4$— | " | 193–195 | | 99 |
| II/28 | p-CN—C$_6$H$_4$ | " | 197–199 | | 100 |
| II/29 | m-Cl—C$_6$H$_4$— | " | 138–140 | | 99 |
| II/30 | —CH=CH$_2$ | 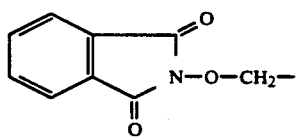 | 58–61 | | 98 |
| II/31 | —CH$_2$—OCH$_3$ | " | 91–93 | | 80 |
| II/32 | —COOCH$_2$—CH$_3$ | " | 85–91 | | 98 |
| II/33 | —CH$_2$—C$_6$H$_5$ | " | | 3.05(t), 4.40(t), 7.20–7.38(m), 7.87(s) | 91 |
| II/34 | —CH$_2$—CH=CH$_2$ | " | | 2.43–2.53(m), 4.20(t), 5.08(dd), 5.21(dd), 5.81–5.99(m), 7.87(s) | 73 |
| II/35 | —C≡CH | " | 150–151 | | 99 |

TABLE I-continued

| Intermediate No. | R | [structure: 5-membered ring with N—O—CH₂— and two C=O groups] | m.p. [°C.] | ¹H-NMR | Yield [%] |
|---|---|---|---|---|---|
| II/36 | trans-CH=CHCH₃ | " | 109-113 | 1.65(d), 4.59(d), 5.66-5.85(m), 7.89(s) | 97 |
| II/37 | 2-(5-Chloro-thienyl) | " | | 5.28(s), 7.05(d), 7.16(d), 7.85(s) | 98 |
| II/38 | 3,4-Cl₂—C₆H₃— | " | 181-183 | | 99 |
| II/39 | 4-CH₃O—C₆H₄— | " | 140-142 | | 98 |
| II/40 | 3-CF₃—C₆H₄— | " | 105-106 | | 98 |
| II/41 | 4-Cl—C₆H₄— | " | 136-137 | | 99 |
| II/42 | N≡C— | " | 141-145 | | 82 |
| II/43 | Phenyl | [6-membered ring with N—O—CH₂— and two C=O groups] | 133-136 | | 87 |
| II/44 | Phenyl | [4-membered ring with N—O—CH₂— and two C=O groups] | 140-142 | | 97 |

Preparation of the O-substituted hydroxylamines I

EXAMPLES 1 to 6

170 millimoles of the imidoether II in 75 ml of 2-aminoethanol are kept at 60° C. for 2 hours. The reaction mixture is poured into water and the product extracted with methylene chloride, after which working up is carried out in a conventional manner.

The results are summarized in Table 2.

EXAMPLE 7

Preparation of tert-butyl aminooxyacetate (compound 7)

230 g (3.8 moles) of 2-aminoethanol are added to 1.06 kg (3.8 moles) of tert-butyl N-phthalimidooxyacetate in 2 l of diethyl ether. The mixture is refluxed for 4 hours, the cleavage product is filtered off under suction and the residue is distilled (41°-42° C., 0.4 mmHg). The yield is 80%; ¹H NMR (CDCl₃): δ=1.49 (s), 4.13 (s), 5.85 (s, broad).

| | | H₂N—O—CH₂—R | | Compounds I |
|---|---|---|---|---|
| Example No. Compound No. | Intermediate No. | R | ¹H-NMR [ppm] | Yield [%] |
| 1 | II/8 | 4-Chlorobenzyl | 2.85(t), 3.84(t), 5.37(s, broad), 7.11(d), 7.22(d) in CDCl₃ | 83 |
| 2 | II/4 | 2-Tetrahydrofuryl | 1.53-2.00(m), 3.60-4.00(m), 4.09-4.12(m), 5.57(s, broad) in CDCl₃, | 67 |
| 3 | II/33 | Benzyl | 2.80(t), 3.70(t), 5.98(s), 7.13-7.31(m), | 98 |
| 4 | II/37 | 2-(5-Chlorothienyl) | 4.71(s), 5.48(s, broad), 6.80(m) | 90 |
| 5 | II/19 | [structure: N=N ring with two C(CH₃) groups and O] | 1.41(d), 3.21(m), 4.84(s), 5.82(s, broad) | 82 |
| 6 | II/19 | [structure: dioxolane-type ring with CH₃] | 1.28(d), 1.32(d), 1.90-2.00(m), 3.32-3.42(m), 3.78-3.88(m), 4.09-4.27(m), 5.00-5.12(t), 5.48(s) | 85 |

EXAMPLE 8

Preparation of 2,2-diethoxyethoxyamine (compound 8)

N-(diethoxyethoxy)-phthalimide is converted and the mixture worked up, these steps being carried out similarly to Example 7. Compound 8 is obtained as an oil in 96% yield. $^1$H NMR (CDCl$_3$): $\delta = 1.22$ (t), 1.22 (t), 3.53–3.64 (m), 3.73 (m), 4.74 (t), 5.60 (s).

Preparation of salts of the O-substituted hydroxylamines I

The results are summarized in Table 3.

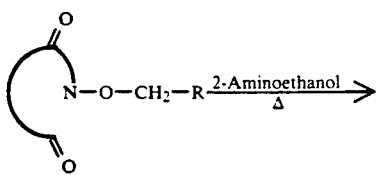

TABLE 3

Salts of the compounds I H$_2$N—O—CH$_2$—R × (HCl)$_q$

| Example No. Compound No. | R | q | m.p. [°C.] | $^1$H-NMR [ppm] | Yield [%] |
|---|---|---|---|---|---|
| 9 | p-F—C$_6$H$_4$— | 1 | 232–234 | | 95 |
| 10 | o-F—C$_6$H$_4$—O—CH$_2$— | 1 | 170–172 | | 92 |
| 11 | p-CH$_3$—C$_6$H$_4$— | 1 | 211–213 | | 90 |
| 12 | p-NO$_2$—C$_6$H$_4$— | 1 | 202–204 | | 89 |
| 13 | p-CN—C$_6$H$_4$— | 1 | 192–195 | | 87 |
| 14 | m-Cl—C$_6$H$_4$— | 1 | 194–198 | | 94 |
| 15 | —CH$_2$—O—CH$_3$ | 1 | | 3.29(s), 3.57(t), 4.19(t), 11.21(s, broad) | 95 |
| 16 | Cyclopropyl | 1 | 150–151 | | 81 |
| 17 | —CH$_2$—O-(2-Naphthyl) | 1 | 200–202 | | 82 |
| 18 | m-CF$_3$—C$_6$H$_4$—O—CH$_2$— | 1 | 114–117 | | 83 |
| 19 | —CH$_2$—CH$_2$—CH$_2$—O—CH$_2$—CH$_3$ | 1 | 98–100 | | 84 |
| 20 | m-Cl—C$_6$H$_4$—S—CH$_2$— | 1 | 148–150 | | 90 |
| 21 | (Z)-CH=CHCl | 1 | 175–176 | | 98 |
| 22 | (E)-CH=CHCl | 1 | 177–179 | | 97 |
| 23 | 2,2-(Dichlorocyclopropyl) | 1 | | 1.60(t), 1.84(dd), 2.10–2.26(m), 4.05(dd), 4.28(dd), 11.27(s, broad) | 82 |
| 24 | —CH$_2$—F | 1 | 190–191 | 4.27(dd), 4.39(dd), 4.57(dd), 4.77(dd), 11.27(s, broad) | 91 |
| 25 | o-Cl—C$_6$H$_4$—O—CH$_2$— | 1 | 172–174 | | 87 |
| 26 | m-Cl—C$_6$H$_4$—O—CH$_2$— | 1 | | 4.30(m), 4.44(m), 6.93–7.07(m), 7.33(t), 11.30(s, broad) | 88 |
| 27 | —CH$_2$—CH=CH$_2$ | 1 | 141–143 | | 76 |
| 28 | trans-CH=CH—CH$_3$ | 1 | 158–160 | 1.71(d), 4.48(d), 5.50–5.64(m), 5.83–6.00(m), 11.09(s, broad) | 93 |
| 29 | m-CF$_3$—C$_6$H$_4$— | 1 | 163–165 | | 95 |
| 30 | p-Cl—C$_6$H$_4$— | 1 | 219–220 | | 98 |
| 31 | p-Methoxy-C$_6$H$_4$— | 1 | 190–191 | | 90 |
| 32 | 3,4-Dichloro-C$_6$H$_3$ | 1 | 183–185 | | 89 |
| 33 | 2,6-Dichloro-C$_6$H$_3$ | 1 | 196–199 | | 91 |
| 34 | -Cyclohexyl | 1 | 174 | | 89 |
| 35 | —CN | 1 | 114–116 | | 85 |
| 36 | —CH$_2$—CH$_2$—CN | 1 | 138–140 | | 89 |
| 37 | —CONH$_2$ | 1 | 132–135 | | 81 |
| 38 | Pyrid-3-yl | 2 | 187–188 | | 70 |
| 39 | —CH$_2$CH$_3$ | 1 | 164–165 | | 85 |
| 40 | 2-Phenoxyethyl | 1 | 119–120 | | 87 |
| 41 | —C≡CH | 1 | 163–164 | | 79 |
| 42 | (4-Phenoxy-phenoxy)-methyl | 1 | 183–184 | | 91 |
| 43 | —CH(CH$_3$)$_2$ | 1 | 126–128 | | 82 |
| 44 | m-F—C$_6$H$_4$— | 1 | 204–206 | | 98 |
| 45 | o-F—C$_6$H$_4$— | 1 | 177–178 | | 97 |
| 46 | 3-Phenoxy-n-propyl | 1 | 177–178 | | 95 |
| 47 | m-NO$_2$—C$_6$H$_4$ | 1 | 172–175 | | 85 |
| 48 | H$_2$N—O—CH$_2$— | 2 | 218–220 | | 93 |
| 49 | H$_2$N—O—CH$_2$—CH=CH— | 2 | 176–180 | | 91 |

EXAMPLES 9 to 49

Preparation of the hydrochlorides of the hydroxylamines I 2.4 moles of 2-aminoethanol are added to a solution of 2.2 moles of an imidoether II and 1.5 liters of ethyl acetate, and the mixture is stirred for 3–4 hours at 60° C. Thereafter, the mixture is cooled to 10° C., N-(hydroxyethoxy)-phthalimide being precipitated and isolated. Hydrogen chloride gas is passed into the filtrate. The resulting precipitate of the O-substituted hydroxylamine hydrochloride is worked up in a conventional manner.

Preparation of the oxalates of the hydroxylamines I

EXAMPLE 50

18.4 g (60 millimoles) of o-chlorophenylethoxyphthalimide in 27 ml of 2-aminoethanol are stirred for 4 hours at 50° C. After dilution with 200 ml of ethyl acetate, the solution is washed with three times 100 ml of water and dried over sodium sulfate. 11.3 g (125.5 millimoles) of oxalic acid, dissolved in 100 ml of ethyl acetate, are added dropwise to the ice-cooled filtrate, the mixture is stirred for 10 minutes at room temperature, and the product is filtered off under suction and washed with ethyl acetate. The yield of compound 50 is 89% and its melting point is 120°–122° C.

EXAMPLE 51

The oxalate is prepared from p-chlorobenzyloxyphthalimide similarly to Example 50. O-p-chlorobenzylhydroxylamine oxalate (compound 51) is obtained in 98% yield and has a melting point of 143° C.

The compounds 52 and 53 are prepared similarly to Example 50 and 51. The results are summarized in Table 4.

TABLE 4

| Example no. Compound no. | H$_2$N—O—CH$_2$—R × (COOH)$_2$ R | mp. [°C.] | Yield [%] |
|---|---|---|---|
| 52 | 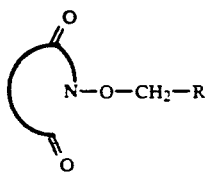 | 106–111 | 67 |
| 53 | CH$_3$—C≡C— | 114–117 | 72 |

We claim:
1. A process for the preparation of an O-substituted hydroxylamine of the formula I

$$H_2N-O-CH_2-R \quad (I)$$

wherein R is a member of the group consisting of: hydrogen, methyl, ethyl, n-propyl, isopropyl, n-butyl, isobutyl, tert-butyl, hexyl, octyl, decyl, dodecyl, tridecyl, ethenyl, 1-propenyl, 2-propenyl, butenyl, hexenyl, ethynyl, propargyl, methoxymethyl, methoxyethyl, methoxypropyl, ethoxymethyl, ethoxyethyl, ethoxybutyl, trifluoromethyl, fluoromethyl, 1-fluoroethyl, chloroethyl, chloroethenyl, fluoroethenyl, bromoethenyl, cyclopropyl, cyclopentyl, cyclohexyl, cyclooctyl, 2,2-dichlorocyclopropyl, phenyl, naphthyl, p-fluorophenyl, p-tolyl, p-nitrophenyl, p-cyanophenyl, m-chlorophenyl, p-methoxyphenyl, m-trifluoromethylphenyl, p-chlorophenyl, 3,4-dichlorophenyl, 2,6-dichlorophenyl, 3-pyridyl, 5-isopropyl-1,3,4-oxadiazol-2-yl, 5-chlorothien-2-yl, 5-methylthien-2-yl, benzyl, p-fluorobenzyl, p-methylbenzyl, p-nitrobenzyl, p-cyanobenzyl, o-chlorobenzyl, m-chlorobenzyl, p-chlorobenzyl, phenoxymethyl, phenoxyethyl, phenoxybutyl, phenoxyhexyl, o-fluorophenoxymethyl, m-trifluoromethylphenoxymethyl, o-fluorophenoxyethyl, m-trifluoromethylphenoxyethyl, O- and m-chlorophenoxyethyl, 2,2-dichlorocyclopropylmethyl, 2-chlorocyclopentylethyl, 2-naphthyloxymethyl, 2-naphthyloxyethyl, phenylthiomethyl, phenylthiobutyl, phenylthiohexyl, m-chlorophenylthiomethyl, m-chlorophenylthioethyl, dimethoxyethyl, diethoxymethyl, diethoxyethyl, diethoxybutyl, diethoxyhexyl, phenylethyl, phenylpropyl, phenylbutyl, phenylhexyl, p- or m-chlorophenylethyl, methylcarboxylate, ethylcarboxylate, isobutylcarboxylate, tertbutylcarboxylate, carboxamide, N-alkylcarboxamide, N,N-dimethylcarboxamide, nitrile, cyanomethyl, 2-cyanoethyl, 2-tetrahydrofuryl, 2tetrahydrofurylmethyl, and 2-tetrahydrofurylbutyl, and its inorganic and organic salts, which consists essentially of reacting a cyclic imidoether II

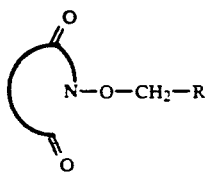

of a 1,4- or 1,5-dicarboxylic acid, with a primary aliphatic aminoalcohol III $$H_2N-A-OH \quad (III)$$

where —A— has the formula —(CH$_2$)$_n$—, —CH$_2$CH(CH$_3$)CH$_2$— or —(CH$_2$CH$_2$O)$_m$—CH$_2$CH$_2$—, wherein m is 1 or 2 and n is 2, 3, or 4, and the compound I is, if required, then converted to its salts.

2. The process of claim 1, wherein, in the case of water-insoluble compounds I, the reaction is carried out using a molar excess of the aminoalcohol III.

3. The process of claim 2, wherein the resulting reaction mixture is extracted with water in order to remove water-soluble components.

4. The process as claimed in claim 1, wherein the reaction of equimolar amounts of the aminoalcohol III and of the imidoether II is carried out in the presence of an inert solvent, and the O-substituted hydroxylamine I is then precipitated as a salt by adding an acid selected from the group consisting of dry hydrogen chloride, anhydrous sulfuric acid, acetic acid, propionic acid, phosphoric acid, malonic acid and benzoic acid.

5. The process of claim 1, wherein water-insoluble O-substituted hydroxylamines of the formula I are prepared using a molar excess of the aminoalcohol III, without converting the compounds of the formula I into their salts.

6. The process of claim 1, wherein the aminoalcohol III is selected from the group consisting of 2-aminoethanol, 3-aminopropan-1-ol, 4-aminobutan-1-ol and 2-(2-aminoethoxy)-ethanol.

7. The process of claim 1, wherein the aminoalcohol III is 2-aminoethanol.

8. The process of claim 4 wherein the acid is dry hydrogen chloride.

* * * * *